(12) United States Patent
Dimalanta et al.

(10) Patent No.: US 7,857,794 B2
(45) Date of Patent: Dec. 28, 2010

(54) HANDPIECE TIP

(75) Inventors: Ramon C. Dimalanta, Rancho Santa Margarita, CA (US); Ziad R. Ghannoum, Trabuco Canyon, CA (US); Sean C. Madden, Mission Viejo, CA (US); Glenn Sussman, Laguna Nigel, CA (US)

(73) Assignee: Alcon, Inc., Hunenberg (CH)

( * ) Notice: Subject to any disclaimer, the term of this patent is extended or adjusted under 35 U.S.C. 154(b) by 1397 days.

(21) Appl. No.: 10/867,195

(22) Filed: Jun. 14, 2004

(65) Prior Publication Data
US 2005/0277898 A1   Dec. 15, 2005

(51) Int. Cl.
*A61M 31/00* (2006.01)

(52) U.S. Cl. .................... 604/275; 604/19; 604/22; 606/39; 606/45

(58) Field of Classification Search .......... 604/275, 604/22, 35, 44, 73, 19; 606/39, 41, 45
See application file for complete search history.

(56) References Cited

U.S. PATENT DOCUMENTS

| | | | |
|---|---|---|---|
| 1,493,450 A | 5/1924 | Richardson | |
| 3,589,363 A | 6/1971 | Banko et al. | |
| 3,606,878 A | 9/1971 | Kellog | |
| 3,818,913 A | 6/1974 | Wallach | |
| 3,930,505 A | 1/1976 | Wallach | |
| 3,994,297 A | 11/1976 | Kopf | |
| 4,024,866 A | 5/1977 | Wallach | |
| 4,169,984 A | 10/1979 | Parisi | |
| 4,223,676 A * | 9/1980 | Wuchinich et al. | ............ 604/22 |
| 4,246,902 A | 1/1981 | Martinez | |
| 4,249,899 A | 2/1981 | Davis | |
| 4,265,618 A | 5/1981 | Herskovitz et al. | |
| 4,301,802 A | 11/1981 | Poler | |
| 4,493,694 A | 1/1985 | Wuchinich | |
| 4,515,583 A | 5/1985 | Sorrich | |
| 4,517,977 A | 5/1985 | Frost | |
| 4,570,632 A | 2/1986 | Woods | |
| 4,577,629 A | 3/1986 | Martinez | |
| 4,589,414 A | 5/1986 | Yoshida et al. | |
| 4,589,415 A | 5/1986 | Haaga | |
| 4,609,368 A | 9/1986 | Dotson | |
| 4,634,419 A | 1/1987 | Kreizman et al. | |
| 4,634,420 A | 1/1987 | Spinosa | |
| 4,643,717 A * | 2/1987 | Cook et al. | ............ 604/22 |
| 4,662,869 A | 5/1987 | Wright | |
| 4,674,502 A | 6/1987 | Imonti | |

(Continued)

FOREIGN PATENT DOCUMENTS

EP   0717970 A1   6/1996

(Continued)

OTHER PUBLICATIONS

Fletcher, et al, "Pulsed liquid microjet for microsurgery", Applied Physics Letters, Mar. 26, 2001, 3 pages, vol. 78, No. 13, p. 1933.

*Primary Examiner*—Nicholas D Lucchesi
*Assistant Examiner*—Quyhn-Nhu H Vu

(57) ABSTRACT

A tip for a surgical handpiece having two coaxial tubes or channels mounted within a body. The tip has one or more features that shape the fluid discharge so as to optimize the performance of the handpiece for varying parts of the surgical procedure.

19 Claims, 2 Drawing Sheets

U.S. PATENT DOCUMENTS

| | | | |
|---|---|---|---|
| 4,696,298 A | 9/1987 | Higgins et al. | |
| 4,706,669 A | 11/1987 | Schlegel | |
| 4,753,234 A | 6/1988 | Martinez | |
| 4,869,715 A | 9/1989 | Sherburne | |
| 4,909,249 A | 3/1990 | Akkas et al. | |
| 4,909,443 A | 3/1990 | Takagi | |
| 4,911,161 A | 3/1990 | Schechter | |
| 4,922,902 A | 5/1990 | Wuchinich et al. | |
| 4,974,581 A | 12/1990 | Wiksell | |
| 4,986,827 A | 1/1991 | Akkas | |
| 4,989,583 A | 2/1991 | Hood | |
| 4,989,588 A | 2/1991 | Kubota et al. | |
| 5,019,035 A | 5/1991 | Missirlian et al. | |
| 5,019,036 A | 5/1991 | Stahl et al. | |
| 5,106,364 A | 4/1992 | Hayafuji et al. | |
| 5,154,694 A | 10/1992 | Kelman | |
| 5,226,910 A | 7/1993 | Kajiyama et al. | |
| 5,250,065 A | 10/1993 | Clement et al. | |
| 5,257,988 A | 11/1993 | L'Esperance, Jr. et al. | |
| 5,261,923 A | 11/1993 | Soares | |
| 5,275,607 A | 1/1994 | Lo et al. | |
| 5,284,472 A | 2/1994 | Sussman et al. | |
| 5,285,795 A | 2/1994 | Ryan et al. | |
| 5,322,504 A | 6/1994 | Doherty et al. | |
| 5,342,293 A | 8/1994 | Zanger | |
| 5,359,996 A | 11/1994 | Hood | |
| 5,380,280 A | 1/1995 | Peterson | |
| 5,413,556 A | 5/1995 | Whittingham | |
| 5,423,330 A | 6/1995 | Lee | |
| 5,554,155 A | 9/1996 | Awh et al. | |
| 5,556,036 A | 9/1996 | Chase | |
| 5,562,692 A | 10/1996 | Bair | |
| 5,591,184 A | 1/1997 | McDonnell | |
| 5,616,120 A | 4/1997 | Andrew et al. | |
| 5,624,392 A | 4/1997 | Saab | |
| 5,624,393 A | 4/1997 | Diamond | |
| 5,634,912 A | 6/1997 | Injev | |
| 5,653,692 A | 8/1997 | Masterson | |
| 5,669,923 A | 9/1997 | Gordon | |
| 5,674,226 A | 10/1997 | Doherty et al. | |
| 5,685,838 A * | 11/1997 | Peters et al. | 604/22 |
| 5,766,194 A | 6/1998 | Smith | |
| 5,807,328 A | 9/1998 | Briscoe | |
| 5,865,790 A | 2/1999 | Bair | |
| 5,873,851 A | 2/1999 | Nilsson et al. | |
| 5,879,347 A | 3/1999 | Saadat | |
| 5,885,243 A | 3/1999 | Capetan et al. | |
| 5,891,095 A | 4/1999 | Eggers et al. | |
| 5,947,988 A | 9/1999 | Smith | |
| 6,039,715 A | 3/2000 | Mackool | |
| 6,126,629 A | 10/2000 | Perkins et al. | |
| 6,132,426 A | 10/2000 | Kroll | |
| 6,135,998 A | 10/2000 | Palanker | |
| 6,139,571 A | 10/2000 | Fuller et al. | |
| 6,146,380 A | 11/2000 | Racz et al. | |
| 6,159,175 A | 12/2000 | Strukel et al. | |
| 6,299,591 B1 * | 10/2001 | Banko | 604/22 |
| 6,340,355 B1 | 1/2002 | Barrett | |
| 6,516,893 B2 | 2/2003 | Pahila | |
| 6,520,929 B2 | 2/2003 | Zaleski | |
| 6,579,270 B2 | 6/2003 | Sussman et al. | |
| 6,871,795 B2 | 3/2005 | Anuskiewicz | |
| 6,902,559 B2 * | 6/2005 | Taufig | 604/542 |
| 6,929,632 B2 * | 8/2005 | Nita et al. | 604/508 |
| 7,014,629 B2 | 3/2006 | Mackool | |
| 2002/0077585 A1 | 6/2002 | Sussman et al. | |
| 2003/0004455 A1 | 1/2003 | Kadziauskas et al. | |
| 2003/0069594 A1 | 4/2003 | Rockley et al. | |
| 2003/0199883 A1 | 10/2003 | Laks | |
| 2003/0208218 A1 | 11/2003 | Kadziauskas | |
| 2004/0068270 A1 | 4/2004 | Allred | |
| 2004/0089080 A1 | 5/2004 | Kadziauskas | |
| 2004/0153093 A1 | 8/2004 | Donovan | |
| 2005/0234473 A1 | 10/2005 | Zacharias | |
| 2006/0047241 A1 | 3/2006 | Boukhny | |
| 2006/0212038 A1 | 9/2006 | Boukhny | |
| 2007/0260173 A1 | 11/2007 | Boukhny et al. | |
| 2008/0167604 A1 | 7/2008 | Hong | |

FOREIGN PATENT DOCUMENTS

| | | |
|---|---|---|
| EP | 1199054 A1 | 4/2002 |
| EP | 1310267 A2 | 5/2003 |
| EP | 1310267 A3 | 5/2003 |
| EP | 1199054 B1 | 5/2004 |
| EP | 1607076 A1 | 12/2005 |
| EP | 1310267 B1 | 1/2008 |
| EP | 1943990 A1 | 7/2008 |
| WO | WO 92/18049 A1 | 10/1992 |
| WO | WO 96/24314 A1 | 8/2006 |

* cited by examiner

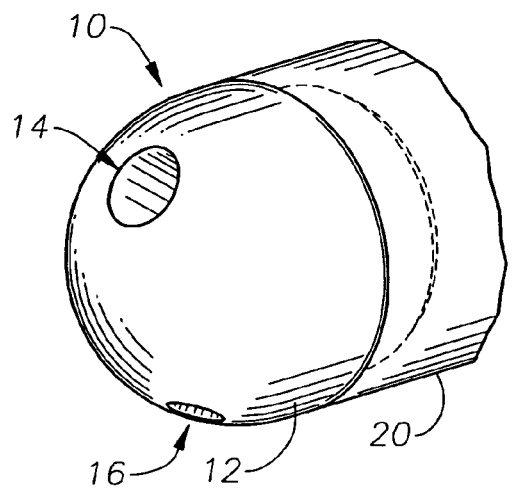
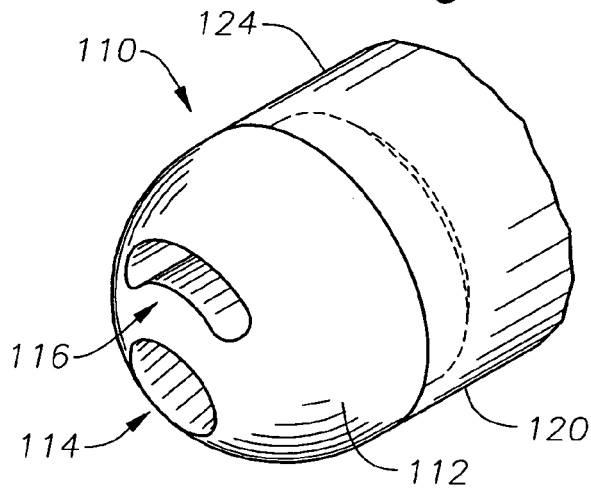
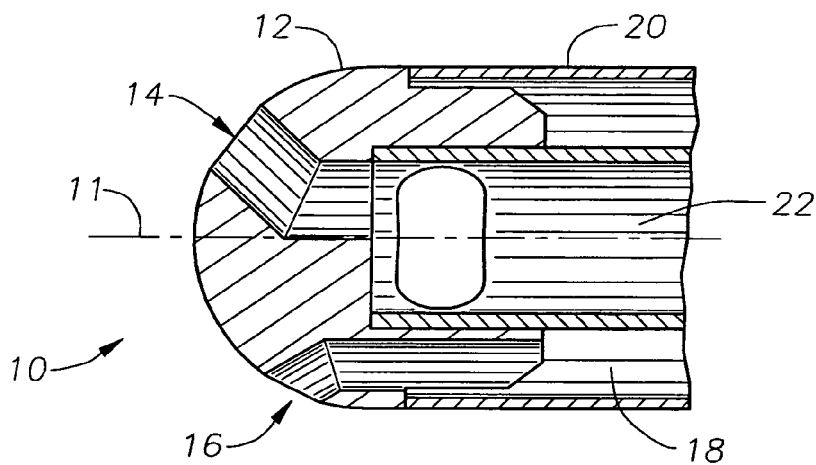
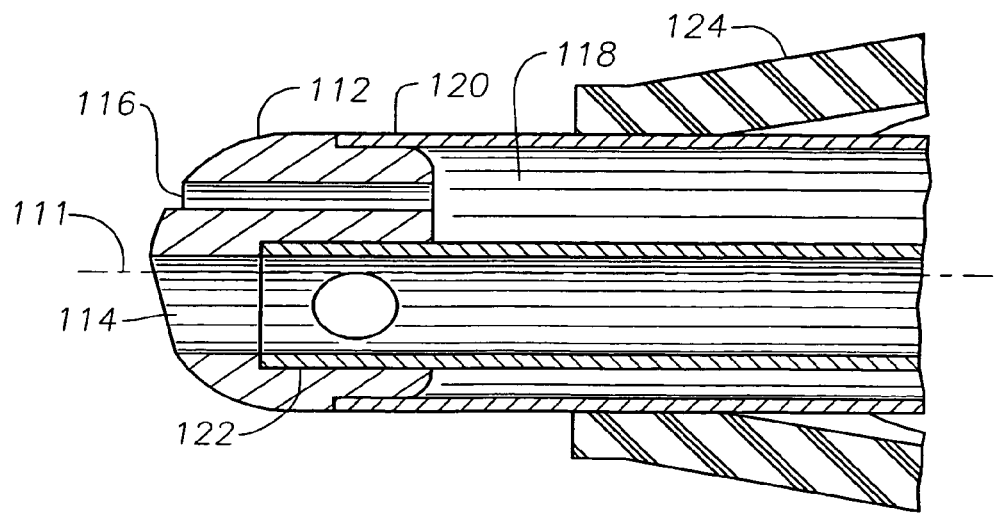

HANDPIECE TIP

BACKGROUND OF THE INVENTION

This invention relates generally to the field of cataract surgery and more particularly to a handpiece tip for practicing the liquefracture technique of cataract removal.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

Recently, a new cataract removal technique has been developed that involves the injection of hot (approximately 45° C. to 105° C.) water or saline to liquefy or gellate the hard lens nucleus, thereby making it possible to aspirate the liquefied lens from the eye. Aspiration is conducted concurrently with the injection of the heated solution and the injection of a relatively cool solution, thereby quickly cooling and removing the heated solution. This technique is more fully described in U.S. Pat. No. 5,616,120 (Andrew, et al.), the entire content of which is incorporated herein by reference. The apparatus disclosed in the publication, however, heats the solution separately from the surgical handpiece. Temperature control of the heated solution can be difficult because the fluid tubes feeding the handpiece typically are up to two meters long, and the heated solution can cool considerably as it travels down the length of the tube.

U.S. Pat. No. 5,885,243 (Capetan, et al.) discloses a handpiece having a separate pumping mechanism and resistive heating element. Such a structure adds unnecessary complexity to the handpiece.

U.S. Pat. No. 6,579,270 B2 (Sussman, et al.) discloses a surgical handpiece and tip having two coaxial tubes or channels mounted within a body. The first tube is used for aspiration and is smaller in diameter than the second tube so as to create an annular passage between the first and second tube. The annular passage communicates with a pumping chamber formed between two electrodes. The pumping chamber works by boiling a small volume of the surgical fluid. As the fluid boils, it expands rapidly, thereby propelling the liquid downstream of the pumping chamber out of the annular passage. The distal end of the annular gap is sealed by a nozzle at the distal ends of the first and second tube and a plurality of orifices or ports may be formed in the nozzle. As the expanding gas is propelled down the annular gap, the gas/liquid stream is forced out of the distal orifice in a controlled and directed manner. However, aspiration and irrigation flow patterns different that those described in this patent are sometimes desired, such as during cortical clean up or posterior capsule washing or lavage.

Therefore, a need continues to exist for a simple surgical handpiece and tip that can heat internally the solution used to perform the liquefracture technique.

BRIEF SUMMARY OF THE INVENTION

The present invention improves upon the prior art by providing a tip for a surgical handpiece having two coaxial tubes or channels mounted within a body. The tip has one or more features that shape the fluid discharge so as to optimize the performance of the handpiece for varying parts of the surgical procedure.

Accordingly, one objective of the present invention is to provide a tip for a surgical handpiece having at least two coaxial tubes.

Another objective of the present invention is to provide a tip for a handpiece having a pumping chamber.

Another objective of the present invention is to provide a tip for a surgical handpiece having a device for delivering the surgical fluid through the handpiece in pulses.

Still another objective of the present invention is to provide a tip for a handpiece that delivers fluid pulses in a controlled and directed manner.

These and other advantages and objectives of the present invention will become apparent from the detailed description and claims that follow.

BRIEF DESCRIPTION OF THE DRAWINGS

FIG. 1 is a partial front, upper left perspective view of a first embodiment of the handpiece tip of the present invention.

FIG. 2 is a partial cross-sectional view of the handpiece tip illustrated in FIG. 1.

FIG. 3 is a partial front, upper left perspective view of a second embodiment of the handpiece tip of the present invention.

FIG. 4 is a partial cross-sectional view of the handpiece tip illustrated in FIG. 3.

DETAILED DESCRIPTION OF THE INVENTION

Figure 5:
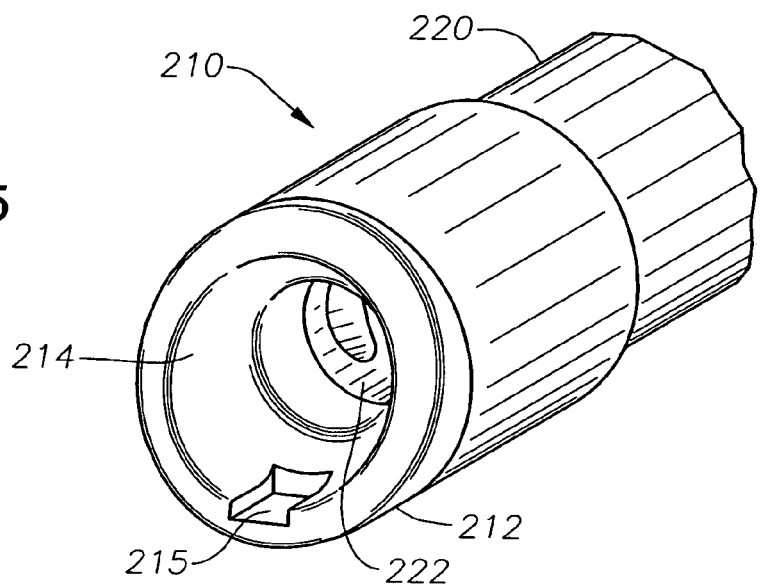
FIG. 5 is a partial front, upper left perspective view of a third embodiment of the handpiece tip of the present invention.

Handpieces suitable for use with the present invention include the INFINITI® AQUALASE® surgical system which is commercially available from Alcon Laboratories, Inc., Fort Worth, Tex. This system uses a tip generally described in FIGS. 23 and 24 and column 7, lines 33-45 of U.S. Pat. No. 6,579,270 B2 (Sussman, et al.) and these portions of such patent are specifically incorporated herein by reference. As described in this patent, tip 900 may alteratively consist of outer tube 965 surrounding and coaxial with inner tube 967. Distal tip 902 of outer tube 965 is flared or belled so as to allow nozzle 905 to be inserted between outer tube 965 and inner tube 967. As best seen in FIG. 23, nozzle 905 contains fluid channel 907 that communicates with orifice 904. Nozzle 905 seals annular gap 969 between outer tube 965 and inner tube 967. Pressurized fluid flowing down annular gap 969 is forced into fluid channel 907 and out orifice 904.

As best seen in FIGS. 1 and 2, in a first embodiment, tip 10 of the present invention generally includes rounded tip cap or body 12 having aspiration port 14 and irrigation port 16. Body 12 seals annular gap 18 between outer irrigation tube 20 and inner aspiration tube 22. Aspiration port 14 is offset at an angle relative to centerline 11 of outer tube 20 and inner tube 22 and irrigation port 16 is likewise offset at an angle relative to centerline 11 of outer tube 20 and inner tube 22. Aspiration port 14 is generally smaller in diameter than inner tube 22. Such a construction directs the pulses of heated fluid exiting irrigation port 16 away from aspiration port 14. Such a construction is particularly useful during the irrigation/aspiration ("I/A") portion of a lens removal surgical procedure, such as cortical clean up.

As best seen in FIGS. 3 and 4, in a second embodiment, tip 110 of the present invention generally includes rounded body 112 having aspiration port 114 and irrigation port 116. Body 112 seals annular gap 118 between outer irrigation tube 120 and inner aspiration tube 122. Tip 110 may also include outer soft silicone sleeve 124 providing a second source of irrigation. Irrigation port 116 is arcuate in shape. Aspiration port 114 and inner aspiration tube 122 are offset from centerline 111 of outer irrigation tube 120. Such a construction directs the pulses of heated fluid exiting irrigation port 16 away from aspiration port 14. Aspiration port 114 is generally smaller in diameter than inner tube 122. Such a construction is particularly useful during the posterior capsule polishing or posterior capsule lavage portion of a lens removal surgical procedure.

Figure 6:
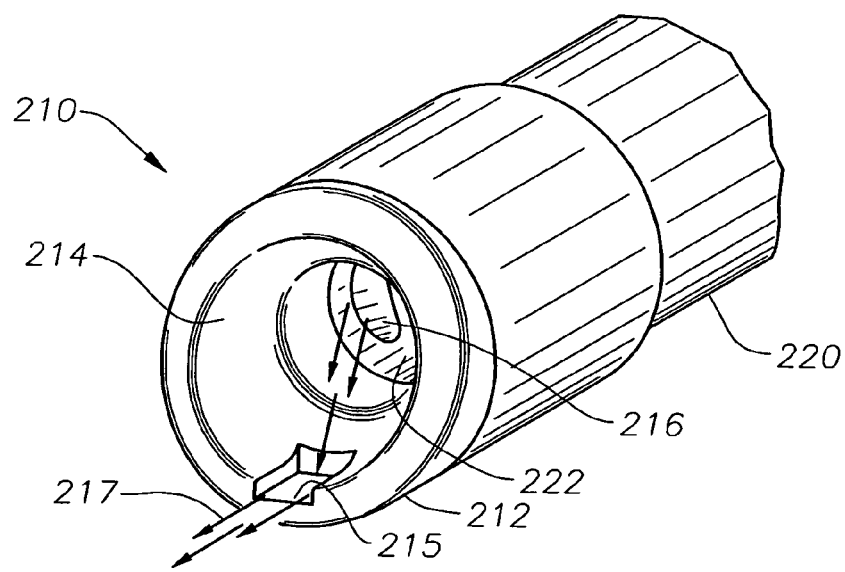
FIG. 6 is a partial front, upper left perspective view of a third embodiment of the handpiece tip of the present invention similar to FIG. 5, but illustrating a fluid stream exiting the tip.
Figure 7:
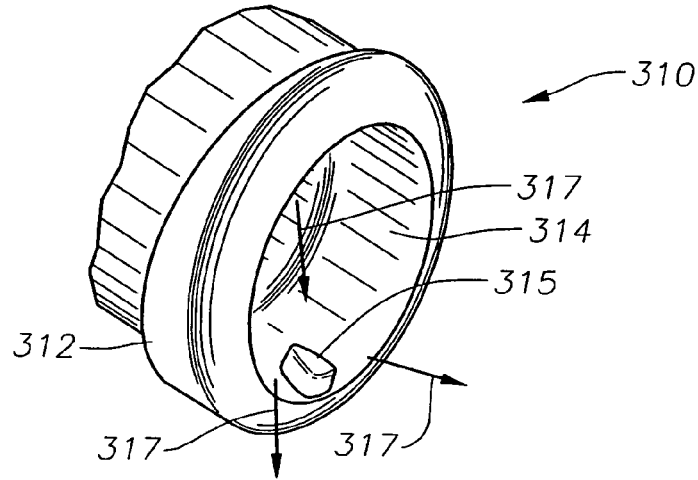
FIG. 7 is a partial front, upper right perspective view of a fourth embodiment of the handpiece tip of the present invention.

As best seen in FIGS. 5 and 6, in a third embodiment, tip 210 has a construct very similar to tip 900 and nozzle 905 as described in U.S. Pat. No. 6,579,270 B2 (Sussman, et al.). Cylindrical body 212 seals the annular gap between outer irrigation tube 220 and inner aspiration tube 222. Aspiration port 214 is cylindrical and located centrally and coaxially with outer irrigation tube 220 and inner aspiration tube 222. Port 214 contains groove or notch 215 against which, fluid exiting nozzle port 216 is directed. As best seen in FIG. 6, such a construction cause fluid 217 exiting tip 210 to be more narrowly focused and not spread out in a fan shaped pattern. One skilled in the art will recognize that notch 215 may be of any desired shape, such as straight-walled (as illustrated in FIGS. 5 and 6), converging or diverging. Alternatively, as seen in FIG. 7, port 314 in body 312 on tip 310 may contain raised obstruction 315 an any suitable size and shape so as to disperse fluid 317 in any desired spray pattern.

This description is given for purposes of illustration and explanation. It will be apparent to those skilled in the relevant art that changes and modifications may be made to the invention described above without departing from its scope or spirit. For example, it will be recognized by those skilled in the art that the present invention may be combined with ultrasonic and/or rotating cutting tips to enhance performance. In addittion, aspiration may or may not be used and the tips of the present invention may be used only as irrigation devices.

We claim:

1. A tip for a handpiece for use in an ophthalmic lens removal procedure, comprising:
    an inner tube mounted within an outer tube so as to form an annular gap between the inner tube and the outer tube; and
    a tip cap sealing distal ends of the inner tube and the outer tube, the tip cap having an aspiration port in fluid communication with the inner tube, and an irrigation port in fluid communication with the annular gap and wherein a centerline of the aspiration port is offset at an angle relative to a centerline of the outer tube and a centerline of the irrigation port is offset relative to a centerline of the outer tube;
    wherein the tip cap comprises a cylindrical side surface and a rounded outer distal surface on an end of the cylindrical side surface and is configured to direct fluid onto the lens from the irrigation port and aspirate fluid from the lens through the aspiration port;
    wherein the aspiration port is a hole in the rounded outer distal surface; and
    wherein the irrigation port is another hole in the rounded outer distal surface;
    wherein the irrigation port is configured to provide irrigation and the aspiration port is configured to provide aspiration for the ophthalmic lens removal procedure.

2. The tip of claim 1, wherein the aspiration port is smaller in diameter than the inner tube.

3. The tip of claim 1, wherein the inner tube is offset relative to the centerline of the outer tube.

4. The tip of claim 1, wherein irrigation fluid exits the tip through the irrigation port.

5. The tip of claim 1, wherein fluid, from an eye, enters the tip through the aspiration port.

6. A tip for a handpiece, comprising:
    an inner tube mounted within an outer tube so as to form an annular gap between the inner tube and the outer tube; and
    a tip cap sealing distal ends of the inner tube and the outer tube, a distal end of the tip cap having an aspiration port in fluid communication with the inner tube, the aspiration port being smaller in diameter than the inner tube, and the distal end of the tip cap having an irrigation port in fluid communication with the annular gap and wherein a centerline of the aspiration port is offset at an angle relative to a centerline of the outer tube and a centerline of the irrigation port is offset at an angle relative to a centerline of the outer tube;
    wherein the centerline of the aspiration port is offset at an angle of less than 90 degrees from the centerline of the outer tube; and
    wherein the centerline of the irrigation port is offset at an angle of less than 90 degrees from the centerline of the outer tube.

7. The tip as recited in claim 1, further comprising an outer silicon sleeve coupled to the tip.

8. The tip as recited in claim 6, wherein the tip cap is configured to direct fluid onto tissue from the irrigation port and aspirate fluid from the tissue through the aspiration port.

9. The tip as recited in claim 6,
    wherein the tip cap comprises a rounded outer surface;
    wherein the aspiration port includes at least one hole in the rounded outer surface; and
    wherein the irrigation port includes at least one other hole in the rounded outer surface.

10. The tip as recited in claim 6, further comprising an outer silicon sleeve coupled to the tip.

11. The tip of claim 6, wherein irrigation fluid exits the tip through the irrigation port.

12. The tip of claim 6, wherein fluid, from an eye, enters the tip through the aspiration port.

13. A tip for a surgical handpiece for removing a lens during cataract removal surgery, comprising:
    an inner tube coupled within an outer tube, wherein an annular gap is formed between the inner tube and the outer tube; and a tip cap coupled over distal ends of the inner tube and the outer tube, the tip cap having an aspiration port in fluid communication with the inner tube, and an irrigation port in fluid communication with the annular gap;

wherein the tip cap comprises a cylindrical side surface and a rounded outer distal surface on an end of the cylindrical side surface and is configured to direct fluid onto the lens from the irrigation port and aspirate fluid from the lens through the aspiration port;

wherein the aspiration port includes at least one hole in the rounded outer distal surface; and wherein the irrigation port includes at least one other hole in the rounded outer distal surfacer; wherein the aspiration port is offset at an angle relative to a centerline of the outer tube; and wherein the irrigation port is offset at an angle relative to a centerline of the outer tube.

14. The tip as recited in claim 13, further comprising an outer silicon sleeve coupled to the tip.

15. The tip as recited in claim 13, wherein the irrigation port is configured to direct fluid at an angle relative to a centerline of the outer tube.

16. The tip of claim 6, wherein the inner tube is offset relative to the centerline of the outer tube.

17. The tip of claim 13, wherein the inner tube is offset relative to the centerline of the outer tube.

18. The tip of claim 13, wherein irrigation fluid exits the tip through the irrigation port.

19. The tip of claim 13, wherein fluid, from an eye, enters the tip through the aspiration port.

* * * * *